US00PP33859P2

(12) United States Plant Patent
Van Swieten

(10) Patent No.: US PP33,859 P2
(45) Date of Patent: Jan. 11, 2022

(54) ***PHALAENOPSIS* ORCHID PLANT NAMED 'PHALEIMXOG'**

(50) Latin Name: ***Phalaenopsis* hybrid**
Varietal Denomination: PHALEIMXOG

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 17/300,548

(22) Filed: Aug. 11, 2021

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./311
See application file for complete search history.

*Primary Examiner* — Susan McCormick Ewoldt
(74) *Attorney, Agent, or Firm* — Jondle & Associates, P.C.

(57) ABSTRACT

A new and distinct variety of *Phalaenopsis* plant named 'PHALEIMXOG', particularly characterized by having light greenish-yellow, striped flowers with small reddish-purple dots at the center and red-purple lips, a compact plant, a medium bump and ridge of the lip, and is propagated by meristem tissue culture, is disclosed.

3 Drawing Sheets

Genus and species: *Phalaenopsis* hybrid.
Variety denomination 'PHALEIMXOG'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALEIMXOG'.

The new *Phalaenopsis* plant is a product of a planned breeding program conducted by the inventor in Bleiswijk, the Netherlands. The objective of this breeding program was to create a new *Phalaenopsis* plant with numerous attractive and small, light greenish-yellow, striped flowers with small reddish-purple dots at the center and red-purple lips, suitable for potted plant production.

The new *Phalaenopsis* plant 'PHALEIMXOG' is a result of cross-pollination made by the inventor in February 2012 in Bleiswijk, the Netherlands, of the proprietary female, or seed parent, *Phalaenopsis* hybrid '01-4155' (unpatented) with the proprietary male, or pollen parent, *Phalaenopsis* hybrid '01-3358' (unpatented).

The new *Phalaenopsis* was selected by the inventor as a single plant within the progeny of the stated cross-pollination in a controlled greenhouse in Bleiswijk, the Netherlands, in March 2015. Asexual reproduction of the new *Phalaenopsis* plant by meristem tissue culture since 2016 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Jan. 30, 2020 (Application no. 2020/0304), by Applicant who obtained the subject matter disclosed directly from the inventor. 'PHALEIMXOG' has not been made publicly available or sold anywhere in the world prior to the effective filing date of this application with the exception of sales or disclosures made one year or less before the effective filing date of this claimed invention by Applicant who obtained 'PHALEIMXOG' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHALEIMXOG' as a new and distinct variety of *Phalaenopsis* plant:

1) Light greenish-yellow, striped flowers with small reddish-purple dots at the center and red-purple lips;
2) Plant is compact; and
3) Bump and ridge of the lip is medium.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in June 2021. Colors in the photographs may differ from the color values cited in the detailed botanical description, which accurately describe the actual colors of the new variety.

DESCRIPTION OF THE NEW VARIETY

Figure 1:
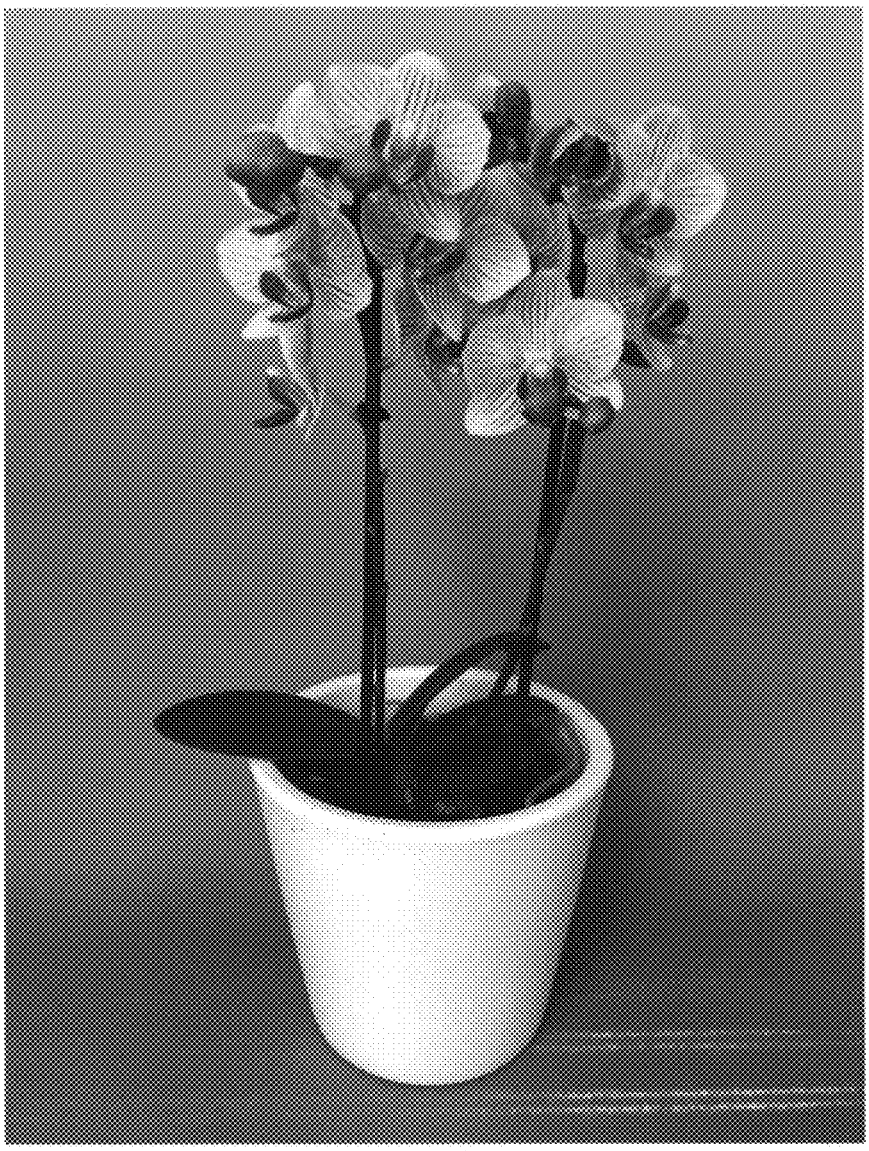
FIG. 1 shows the overall plant habit, including blooms, buds, and foliage of 'PHALEIMIXOG'.
Figure 2:
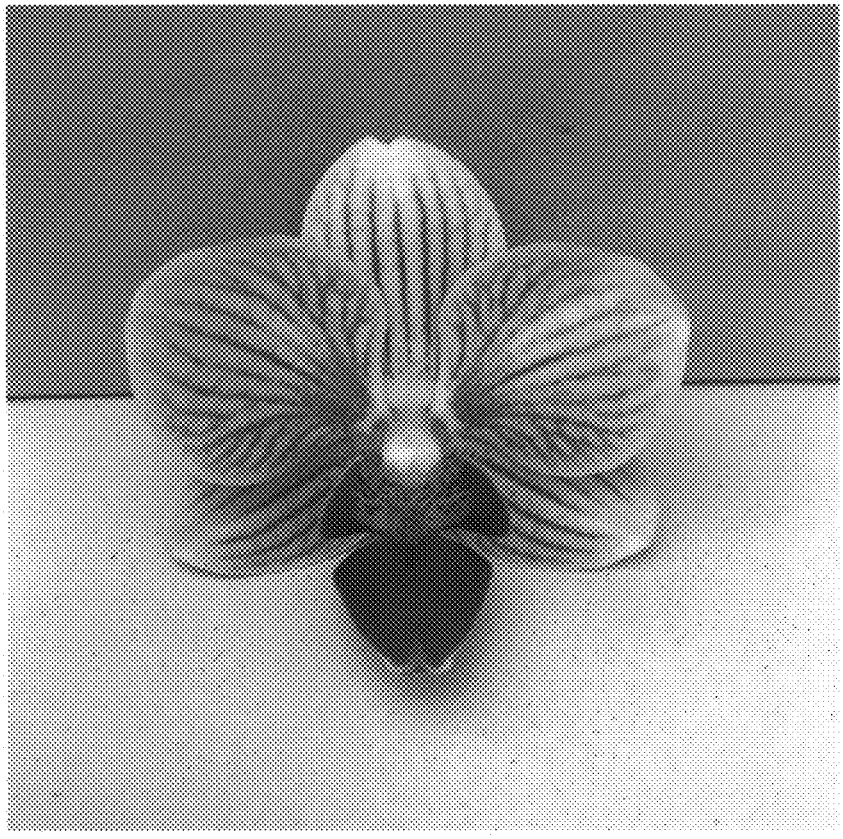
FIG. 2 shows a close-up of a flower of 'PHALEIMXOG'.
Figure 3:
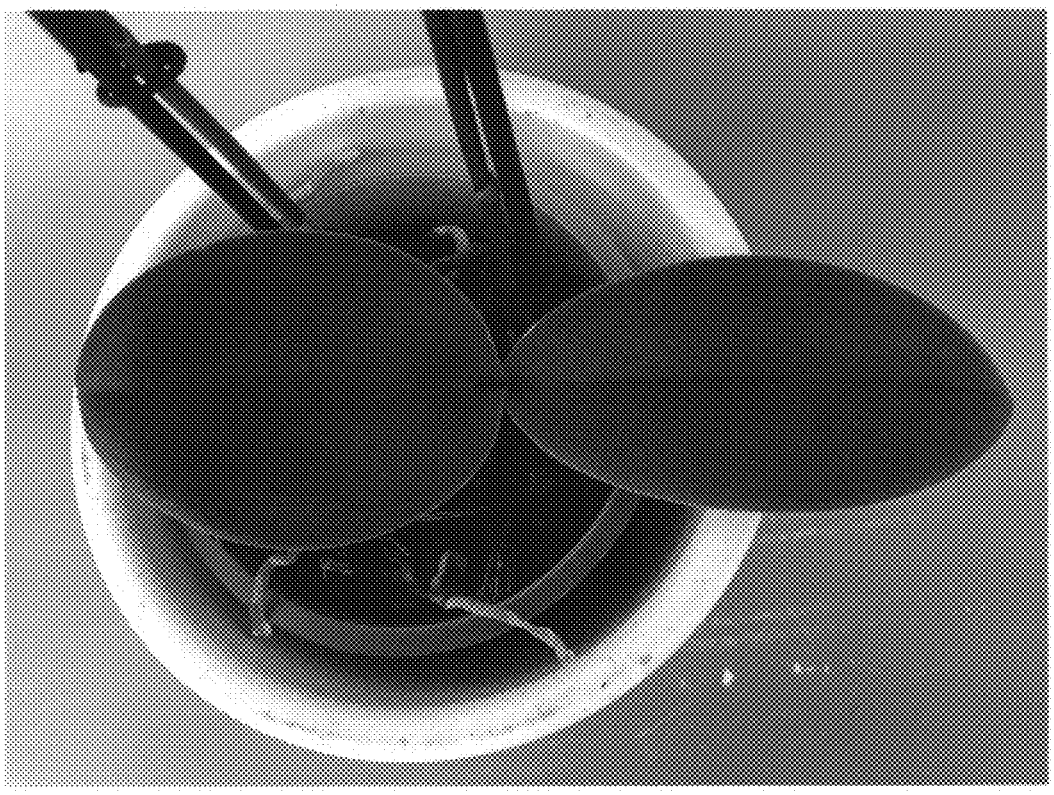
FIG. 3 shows an overhead view of the leaves of 'PHALEIMXOG'.

The following detailed description sets forth the distinctive characteristics of 'PHALEIMXOG'. Plants of the new

*Phalaenopsis* have not been observed under all possible environmental conditions. The phenotype may vary somewhat with variations in environment such as temperature, light intensity, and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in June 2021 on flowering plants which were planted in 12-centimeter (diameter) pots. After in vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family*.—Orchidaceae.

*Botanical*.—*Phalaenopsis* hybrid.

*Common name*.—Moth orchid.

*Variety name*.—'PHALEIMXOG'.

Parentage:

*Female parent*.—*Phalaenopsis* cultivar '01-4155' (unpatented).

*Male parent*.—*Phalaenopsis* cultivar '01-3358' (unpatented).

Propagation:

*Type*.—Meristem tissue culture.

Roots:

*Root description*.—Greyed-green (a color in between RHS 190B and RHS 190C) colored roots with branching lateral roots having yellow-green (RHS 145C) colored root tips.

Plant:

*Crop time to flowering*.—Following asexual propagation (in vitro), the rooted cuttings grow for 20-24 weeks. After transplantation into 12-cm pots, the plants are finished after 48 to 50 weeks.

*Growth habit of the peduncle*.—Upright to slightly pendent with raceme and panicle inflorescence.

*Height* (*from soil level to top of inflorescence*).—Approximately 28.0 cm to 33.0 cm.

*Width* (*measured from leaf tips*).—About 16.0 cm to 18.0 cm.

*Vigor*.—Strong.

Leaves:

*Mature leaves*.—Quantity per plant: 6 to 7 leaves are produced before flowering. Length (fully expanded): 9.0 cm to 11.0 cm. Width: 5.0 cm to 6.0 cm. Position of the broadest part of the leaf: At the middle. Shape: Oblong. Base shape: Slightly elongated. Apex: Obtuse asymmetric. Leaf blade angle with the petiole (measured from the horizontal position): Between 10 degrees and 30 degrees. Leaf margin: Entire. Color: Upper surface: RHS 146A. Lower surface: RHS 146B. Texture (both upper and lower surfaces): Smooth. Thickness: 2.0 mm to 3.0 mm. Variegation: Absent. Venation: Pattern: Parallel. Color of the midvein: Upper surface: RHS 146A. Lower surface: RHS 146B.

Peduncle:

*Quantity per plant*.—1 to 2.

*Number of flowers per peduncle*.—9 to 12.

*Length*.—28.0 cm to 33.0 cm.

*Diameter*.—3.0 mm to 4.0 mm.

*Strength*.—Strong.

*Aspect*.—Upright to slightly pendent.

*Texture*.—Smooth.

*Color*.—Green (RHS 146B) with a touch of brown (RHS N200A).

*Internode length*.—1.5 cm to 2.5 cm.

Inflorescence description:

*Appearance*.—Upright to slightly pendent, raceme and panicle inflorescence with bilaterally symmetrical flowers that open in succession beginning with the lowermost flower.

*Number of inflorescences*.—1 to 2.

*Inflorescence size*.—Height (from base to tip): 130.0 mm to 160.0 mm.

*Flowering time*.—First flowers can be expected 10 to 11 months after planting in a 12-cm pot.

*Flower*.—Height: 50.0 mm to 55.0 mm. Diameter: 52.0 mm to 57.0 mm. Depth of lip: 22.0 mm to 24.0 mm.

*Flower longevity*.—On the plant: 10 to 12 weeks.

*Flower shape*.—Flat.

*Fragrance*.—Absent.

*Flower bud*.—Average size: Medium. Length: 17.0 mm to 19.0 mm. Width: 13.0 mm to 15.0 mm. Shape: Egg shaped. Color: Yellowish-green (RHS N144A) at the base and lighter yellow-green (RHS N144C) toward the tip with dark purplish-red stripes (RHS N79B).

*Petals*.—Arrangement: Open/free. Shape: Semi-circular. Apex: Rounded asymmetric. Margin: Entire. Length (from base to tip): 24.0 mm to 26.0 mm. Width: 24.0 mm to 26.0 mm. Position of the broadest part of the petal: Toward the base. Color (when fully opened): Upper surface: Basic color: Light greenish-yellow (RHS 3C). Over color: Touch of light reddish-purple (RHS N78D) at the base; small reddish-purple dots (RHS N78B) at the base; purplish-red stripes (RHS 61A). Lower surface: Basic color: Light greenish-yellow (RHS 3D). Over color: Very light purple (RHS 76B) at the base and diluting purplish-red stripes (RHS 70A). Number of spots, dots, and stripes on the petals (upper surface): Few to medium dots; medium to many stripes. Color of spots, dots, and stripes on the petals (upper surface): Dots (RHS N78A); stripes (RHS 61A). Density of netting of the petals (upper surface): None. Color of the netting (upper surface): None.

*Dorsal sepal*.—Shape: Elliptic. Apex: Emarginated symmetric. Margin: Entire. Length (from base to tip): 26.0 mm to 28.0 mm. Width: 21.0 mm to 23.0 mm. Position of the broadest part of the dorsal sepals: At the middle. Color (when fully opened): Upper surface: Basic color: Light greenish-yellow (RHS 2C). Over color: Few very small reddish-purple dots (RHS N78B) at the base; purplish-red stripes (RHS 61A). Lower surface: Basic color: Light greenish-yellow (RHS 2C). Over color: Greenish-yellow (RHS 151A) at the middle; diluting purplish-red stripes (RHS 70A). Number of spots, dots, and stripes on the dorsal sepals (upper surface): Medium to many stripes; few small dots at the base. Color of spots, dots, and stripes on the dorsal sepals (upper surface): Stripes (RHS 61A); dots (RHS N78B). Density of netting of the dorsal sepals (upper surface): Low. Color of the netting (upper surface): RHS 61A.

*Lateral sepals*.—Shape: Ovate. Apex: Obtuse asymmetric. Margin: Entire. Length (from base to tip): 27.0 mm to 30.0 mm. Width: 20.0 mm to 22.0 mm. Position of the broadest part of the lateral sepals: Toward the base. Color (when fully opened): Upper surface: Basic color: Light greenish-yellow (RHS 2C). Over color: Purplish-red dots, stripes, and netting (RHS 61A). Lower surface: Basic color: Yellow-green (RHS 151C). Over color: Small diluting dots at the base and stripes (RHS 70A); yellow-green shade and midvein (RHS 150C) toward the tip. Number of spots, dots, and stripes on the lateral sepals (upper surface): Very small dots at the base; medium and medium to many stripes. Color of spots, dots, and stripes on the lateral sepals (upper surface): RHS 61A. Density of netting of the lateral sepals (upper surface): Low. Color of the netting (upper surface): RHS 61A.

*Labellum* (*lip*).—Whiskers: Present, but very short. Length of whiskers: About 1.0 mm. Color of whiskers: White (RHS NN155C). Pubescence on the lip: Absent.

*Lateral lobe*.—Shape: Type IV (as described in the International Union for the Protection of New Varieties of Plants (UPOV) Test Guidelines for *Phalaenopsis*); weakly spatulate. Margin: Slightly undulated. Length: 13.0 mm to 15.0 mm. Width: 6.0 mm to 8.0 mm. Color: Upper surface: Greenish-yellow (a color in between RHS 6C and RHS 6D) at the base; striped (RHS 59B); purplish-red (RHS 59B) on one side toward the margin; yellow margin (RHS 12B) on one side; reddish-purple (a color in between RHS N78A and RHS N78B) toward the other margin and tip. Lower surface: Light greenish-yellow (RHS 5D) at the base; red (a color in between RHS 59A and RHS 59B) on one side toward margin and reddish-purple (RHS N78B) toward margin and the tip. Number of spots and stripes on the lateral lobe: Few to medium stripes. Color of spots and stripes on the lateral lobe: RHS 59A. Density of netting of the lateral lobe: None. Color of the netting: None.

*Apical lobe*.—Shape: Rhombic. Margin: Entire. Length: 14.0 mm to 16.0 mm. Width: 14.0 mm to 16.0 mm. Color: Upper surface: Purplish-red (RHS 59B) at the base with a touch of dark red (RHS 183B) toward margins of wings and reddish-purple (RHS N78A) toward the tip. Lower surface: Greenish-white (RHS 155C) at the middle from base toward whiskers; touch of dark red at wings (RHS 183C); reddish-purple (RHS N78B) toward margins and whiskers. Number of spots and stripes on the apical lobe: None. Color of spots and stripes on the apical lobe: None. Density of netting of the apical lobe: None. Color of the netting: None. Bump and ridge: Medium.

*Callus*.—Average size: Small. Height: 3.0 mm to 4.0 mm. Length: 3.0 mm to 4.0 mm. Width: 2.0 mm to 3.0 mm. Color: Yellow tips (RHS 12A); light greenish-yellow (RHS 4D) on sides; dotted (RHS N79C).

Reproductive organs:

*Column*.—Length: 6.0 mm to 8.0 mm. Diameter: 3.0 mm to 4.0 mm. Color: Light reddish-purple (RHS N78D).

*Pollinia*.—Quantity: 2. Diameter: 0.2 mm to 0.4 mm. Color: Orange-yellow (RHS 23A).

*Ovary*.—Length: 8.0 mm to 10.0 mm. Diameter: 1.8 mm to 2.0 mm.

*Pedicel*.—Length: 22.0 mm to 24.0 mm. Diameter: 2.2 mm to 2.4 mm. Color: Yellow-green (RHS 145A and RHS 145D) with a touch of pinkish-white (RHS N155C) toward the flower. Texture: Smooth.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALEIMXOG' differs from the female parent plant '01-4155' (unpatented) in that 'PHALEIMXOG' has weakly spatulate lateral lobes and flowers that are striped and dotted at the base, whereas '01-4155' has oblong lateral lobes and flowers that are flecked.

'PHALEIMXOG' differs from the male parent plant '01-3358' (unpatented) in that 'PHALEIMXOG' has flowers with a basic color of light greenish-yellow that are flat in lateral view and rhombic apical lobes, whereas '01-3358' has flowers with a basic color of purplish-pink that are concave in lateral view and triangular to ovate apical lobes.

'PHALEIMXOG' is most similar to the commercial *Phalaenopsis* plants named 'PHALYPBE' (U.S. Plant Pat. No. 33,120) and 'PHALCOFAAK' (unpatented). 'PHALEIMXOG' differs from the commercial variety 'PHALYPBE' in that 'PHALEIMXOG' has whiskers that are white and columns that are light reddish-purple, whereas 'PHALYPBE' has whiskers that are purplish-pink at the base and white toward the tips and columns that are very light purple at the base with white tips.

'PHALEIMXOG' differs from the commercial variety 'PHALCOFAAK' in that 'PHALEIMXOG' has white whiskers and rhombic apical lobes, whereas 'PHALCOFAAK' has reddish-purple whiskers and ovate apical lobes.

I claim:

1. A new and distinct variety of *Phalaenopsis* plant named 'PHALEIMXOG', substantially as described and illustrated herein.

* * * * *